(12) United States Patent
Klibanov et al.

(10) Patent No.: US 6,245,318 B1
(45) Date of Patent: *Jun. 12, 2001

(54) SELECTIVELY BINDING ULTRASOUND CONTRAST AGENTS

(75) Inventors: Alexander L. Klibanov, St. Louis; Leon R. Lyle, Webster Groves; M. Elizabeth Thomas, St. Louis, all of MO (US)

(73) Assignee: Mallinckrodt Inc., St. Louis, MO (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/863,647

(22) Filed: May 27, 1997

(51) Int. Cl.$^7$ ......................................................... A61B 8/00
(52) U.S. Cl. .......................................... 424/9.52; 424/9.51
(58) Field of Search ................................ 424/9.52, 9.51, 424/9.5, 450, 489, 498, 178.1; 516/11, 77; 600/458

(56) References Cited

U.S. PATENT DOCUMENTS

| | | | |
|---|---|---|---|
| 4,853,228 | * | 8/1989 | Wallach et al. ..................... 424/450 |
| 5,498,421 | * | 3/1996 | Grinstaff et al. ..................... 424/450 |
| 5,620,689 | * | 4/1997 | Allen et al. ........................ 424/178.1 |
| 5,643,553 | * | 7/1997 | Schneider et al. .................. 424/9.52 |
| 5,656,211 | * | 8/1997 | Unger et al. .......................... 264/4.1 |

FOREIGN PATENT DOCUMENTS

| | | | |
|---|---|---|---|
| 727225 | * | 2/1996 | (EP) .............................. A61K/49/00 |
| 727225 A2 | * | 8/1996 | (EP) .............................. A61K/49/00 |

* cited by examiner

Primary Examiner—Diana Dudash
Assistant Examiner—Michael G. Hartley
(74) Attorney, Agent, or Firm—Wendell Ray Guffey; Lawrence L. Limpus

(57) ABSTRACT

The invention discloses an ultrasound contrast media comprising a microbubble shell and a composition of the general formula:

A-P-L, wherein A is an ultrasound contrast agent microbubble-shell binding moiety; P is a spacer arm; and L is a ligand. The present invention discloses compositions, methods of imaging, and methods for attachment of targeting ligands to USCM agents, allowing selective targeting of USCM agents to desired sites.

36 Claims, No Drawings

SELECTIVELY BINDING ULTRASOUND CONTRAST AGENTS

FIELD OF THE INVENTION

The invention is in the field of imaging. In particular, the invention is in the field of ultrasound imaging.

BACKGROUND OF THE INVENTION

Use of ultrasound in medical imaging has greatly increased during the past few decades. Currently, this method of diagnostic imaging is widespread and inexpensive; reasonable quality real-time images of internal organs can be obtained. Ultrasound imaging systems are small, mobile and have low cost. A general disadvantage of this modality in comparison with nuclear medicine and magnetic resonance imaging (MRI) techniques is its lower specificity. In many instances medical ultrasound is unable to distinguish between normal and diseased tissues.

A major improvement was achieved with the recent introduction of the ultrasound contrast materials, which could be used to aid delineation of blood/tissue boundaries and help visualize blood flow and blood supply in various organs. The most efficient ultrasound contrast materials are gas microbubbles, which are strong scatterers of ultrasound. Microbubble dispersions can be administered to the patient intravenously or by other routes. Subsequent to administration, the microbubble-containing tissues of the body are visible on the screen of the imaging system as bright areas. However, even with the use of these contrast materials, selective enhancement of certain diseased tissues for ultrasound imaging is still far from clinical application. This task of selective enhancement might be achieved with targeted ultrasound contrasts.

Targeting of various contrast agents used for other imaging modalities has been performed for decades. Small molecules, macromolecules, polymers and particles have been successfully delivered to target sites for specific enhancement of the diseased tissue images. Such imaging agents have slowly made their way into clinical practice. Targeted ultrasound contrast agents, which could selectively bind to the specific sites after in vivo administration, were postulated more than a decade ago. Still, commercially successful targeted ultrasound contrast agents have yet to be reported.

It would be beneficial to design a targetable microbubble ultrasound contrast agent that would selectively bind to the areas of interest in the body and enhance the target contrast in the ultrasound examination.

SUMMARY OF THE INVENTION

The invention discloses an ultrasound contrast agent comprising a monolayer microbubble-shell and a composition of the general formula:

A-P-L, wherein A is an ultrasound contrast agent microbubble-shell binding moiety; P is a spacer arm; and L is a ligand.

The present invention discloses compositions, methods of imaging, and methods for attachment of targeting ligands to ultrasound contrast agents, allowing selective targeting of agents to desired sites.

DETAILED DESCRIPTION OF THE INVENTION

Previously, attachment of targeting ligands to ultrasound contrast agents was not performed via flexible polymer chain anchors. Direct coupling via chemical crosslinking agents was typically performed in accordance with standard protein-polymer or protein-lipid attachment methods (e.g., via carbodiimide (EDC) or thiopropionate (SPDP)).

An advantage of the disclosed invention is the availability of the targeting ligand to accommodate conformation of the receptor at the binding site or sites, due to flexibility of the spacer arm. Also, the ligand is spatially separated from the particle; thus reducing steric hindrance for binding to the target from the bulky ultrasound contrast agent particle. This spatial separation improves targeting efficacy. Also, more than one type of ligand may be used with the invention, allowing a cocktail approach to binding numerous targets.

The invention allows multipoint cooperative interaction between a microbubble and target, and will help to accommodate ligand-receptor interaction in the most favorable conformation, allowing stronger binding of the microbubble to the target. Use of the A-P-L design will compensate for the irregularities of the shape of the target, which will otherwise make target receptor molecules on its surface inaccessible for the ligand to be directly immobilized on the surface of the microbubble.

Spacer arms for use with the invention include a branched or linear synthetic polymer or a biopolymer like polyethyleneglycol (PEG), polyvinylpyrrolidone, polyoxyethylene, polyvinylpyridine, polyvinyl alcohol, polyglycerol, dextran, and starch. Such lipid-PEG-ligand compounds have been used for the attachment of ligands to liposomes (bilayer of lipids). In a lipid monolayer-coated gas microbubble of the invention the lipid molecules will be facing the gas phase so the anchor will be deposited at the gas-liquid interface, the polymer spacer arm will be extended in the aqueous medium in order to allow improved interaction of the ligand with the target surface. Unlike the case of liposomes, where a lipid bilayer is formed with the lipid residues facing each other, in the monolayer-coated gas bubble of the invention the lipid molecules face the gas phase. The anchor will be deposited at the gas-liquid interface, and the flexible polymer spacer arm will be extended in the aqueous medium allowing improved interaction of the ligand with the target surface. A flexible spacer arm can provide advantages and the polymers, when used, generally will have over ten monomer residues. Other hydrophilic polymers are proposed as liposome coatings in Torchilin V. P., Shtilman M. I., Trubetskoy V. S., Whiteman K., Milstein A. M., *Biochim.Biophys.Acta*, 1994, 1195:181–184.; Maruyama K., Okuizumi S., Ishida O. et al., *International J. Pharmaceutics*, 1994, 111:103–107; and Woodle M. C., Engbers C. M., Zalipsky S., *Bioconjugate Chemistry*, 1994, 5:493–496.

The ultrasound contrast agent monolayer microbubble-shell-binding groups for use with the invention include lipids, phospholipids, long-chain aliphatic hydrocarbon derivatives, lipid multichain derivatives, comb-shaped lipid-polymer derivatives (usually including hydrophobic residues attached), steroids, fullerenes, polyaminoacids, native or denatured proteins, albumin, phosphatidylethanolamine (e.g., distearoyl phosphatidylethanolamine), cardiolipin, aromatic hydrocarbon derivatives, and partially or completely fluorinated lipid derivatives. It is preferable to have larger-size derivatives which would be difficult to remove from the bubble surface gas-liquid interface. Spreading and/or intermolecule binding at the monolayer interface (e.g., covalent, ionic or hydrogen bonding or van der Waals forces) could be used to further strengthen the anchoring of the ligand on the microbubble shell.

The ligand for use with the invention can be a biomolecule. Biomolecule refers to all natural and synthetic molecules that play a role in biological systems. Biomolecules include hormones, amino acids, vitamins, peptides, peptidomimetics, proteins, deoxyribonucleic acid (DNA) ribonucleic acid (RNA), lipids, albumins, polyclonal antibodies, receptor molecules, receptor binding molecules, monoclonal antibodies, carbohydrates and aptamers. Specific examples of biomolecules include insulins, prostaglandins, cytokines, chemokines, growth factors including angiogenesis factors, liposomes and nucleic acid probes. The advantages of using biomolecules include enhanced tissue targeting through specificity and delivery. Coupling of the chelating moieties to biomolecules can be accomplished by several known methods (e.g., Krejcarek and Tucker *Biochem. Biophys. Res. Comm,* 30, 581 (1977); Hnatowich, et al. *Science,* 220, 613 (1983). For example, a reactive moiety present in one of the R groups is coupled with a second reactive group located on the biomolecule. Typically, a nucleophilic group is reacted with an electrophilic group to form a covalent bond between the biomolecule and the chelate. Examples of nucleophilic groups include amines, anilines, alcohols, phenols, thiols and hydrazines. Electrophilic group examples include halides, disulfides, epoxides, maleimides, acid chlorides, anhydrides, mixed anhydrides, activated esters, imidates, isocyanates and isothiocyanates. Biomolecules can be covalently or noncovalently attached to one of the tips of the polymer chain, while the lipid anchor grouping is attached to the other end of this polymer chain.

A specific example of using the claimed invention is tumor targeting. Ligands designed to bind specifically to receptors for angiogenesis factors expressed in tumor microvasculature and coupled to echogenic contrast agents enhance the specificity and sensitivity of ultrasound tumor detection. Angiogenesis is a process associated with tumor growth. Several peptides have been identified as promoters of angiogenesis including interleukins 8, and 6, acidic FGF, basic FGF, TNF-alpha, TGF-alpha, TGF-beta, and VEGF/ VPF. See Rak, J. W.; St. Croix B.D. and Kerbel R. S. (1995), *Anti-Cancer Drugs* 6, p. 3–18. See also Bicknell, R. (1994), *Annals of Oncology* 5 (Suppl. 4), p. 545–550. Since angiogenesis is a process not generally carried out in the body except during wound healing and a few other specialized circumstances, ligands designed from angiogenesis factors will selectively target tumor vasculature with high specificity. A specific ligand useful for targeting tumor vasculature is the chemokine IL-8 or an analog, homolog, derivative or fragment thereof, or a peptide having specificity for a receptor of interluekin 8. Particularly useful are the amino acid residues at the N terminal end of IL-8, including the "ELR" sequence gluleu-arg found immediately before the initial cysteine residue. It is known that the ELR amino acid sequence of IL-8 is important for the binding interaction with its receptor. The ELR motif also apparently imparts the angiogenic properties of IL-8. See Strieter, R. M.; Kunkel, S. L.; Palverini, P. J.; Arenberg, D. A.; Waltz, A.; Opdenakker, G. and Van Damme, J. (1995), *Journal of Leukocyte Biology* 576, p. 752–762. For the complete sequence of IL-8 see U.S. Pat. No. 5,436,686 Sep. 13, 1994, incorporated herein by reference.

Monolayer microbubble-shells include any composition suitable for ultrasound imaging and capable of being gas filled, liquid filled, or combinations of gas and liquid, and includes those with a protein shell, natural polymer shell, synthetic polymer shell, surfactant, lipid, phospholipid, sphingolipid, sulfolipid, oligolipid, polymeric lipid, sterol, terpene, fullerene, wax, or hydrocarbon shell or any combination of these.

Gases, liquids, and combinations thereof suitable for use with the invention include decafluorobutane, dctafluorocyclobutane, decafluoroisobutane, octafluoropropane, octafluorocyclopropane, dodecafluoropentane, decafluorocyclopentane, decafluoroisopentane, perfluoropexane, perfluorocyclohexane, perfluoroisohexane, sulfur hexafluoride, and perfluorooctaines, perfluorononanes; perfluorodecanes, optionally brominated.

Generally, in making microbubbes, an aqueous dispersion of phospholipid (DSPC), surfactant (PEG stearate) and biotinamidocaproyl PEG-DSPE are mixed in an organic solvent, then the solvent evaporated and saline added. After that, the mixture is generally blended (e.g. sonication, colloid mill) in order to create an aqueous dispersion of the components, and then blending is continued in the presence of the flow of a gas such as decafluorobutane gas, which is dispersed in the form of microbubbles in the aqueous phase. At that moment, DSPC, PEGstearate and Bac-PEG-DSPE are deposited on the gasaqueous interface, with hydrophobic residue facing the gas phase and hydrophilic part of the molecule (including the ligand part) immersed in the aqueous phase. In such a way, the whole surface of the microbubble formed is covered by these molecules which thus create a protective shell.

Next, the microbubbles are purified from the aqueous dispersion such as by flotation: due to the fact that gasfilled microbubbles are much less dense than water, they will float to the top of solution. After that, the aqueous phase is aspirated and replaced with fresh saline which does not contain the shell material, or contains the shell material without the targeting ligand. Centrifugation speeds up the flotation process. This step is employed to remove biotinylated material from solution, otherwise it may block the avidin binding sites. In that case, no biotin-mediated binding of microbubbles may occur. Optionally, ligand-PEG-PE may be added as an aqueous solution to preformed microbubbles, so that the anchor will incorporate in the preformed microbubble shell. One example of a composition of the invention would include biotinamidocaproyl-poly (ethyleneglycol)distearoylphosphatidylethanol amine, Sialyl Lewis-poly (ethylene glycol) phosphatidylethanolamine, Immunoglobulin Fab fragment-(dextran derivative)-cardiolipin, Immunoglobulin Fv fragment-poly(ethylene glycol) phosphatidylethanolamine, SAKELRC-poly (ethylene glycol)phosphatidylethanolamine, and biotinpoly (vinylpyrrolidone)-glycophorin.

Currently, there are three basic strategies for attachment of antibodies or other proteins to PEG-coated liposomes. The first, most obvious method attaches the antibody to the liposome membrane via a lipid anchor, as was done earlier for plain liposomes taught in Maruyama K., Kennel S. J., Huang L., *Proc. Natl. Acad. Sci. USA,* 1990, 87: 5744–5748, Sinha D., Karush F., *Biochem. Biophys. Res. Commun.* 1979, 90, 554–560, Weissig V., Lasch J., Klibanov A. L., Torchilin V. P., FEBS Lett., 1986, 202: 86–90, and Martin F. J., Papahadjopoulos D., *J. Biol. Chem.,* 1982, 257:286–288. An antibody possessing a covalently attached phosphatidylethanolamine derivative has been mixed with lipids and PEG5000-DOPE in octylglucoside aqueous solution, and liposomes have been prepared by a detergent dialysis technique. The resulting long-circulating liposomes demonstrated specific binding to the target in vitro and in vivo. See Klibanov A. L., Maruyama K., Beckerleg A. M., Torchilin V. P., Huang L., *Biochim. Biophys. Acta,* 1991, 1062: 142–148, Mori A., Klibanov A. L., Torchilin V. P., Huang L., *FEBS Lett.,* 1991, 284: 263–266, Klibanov A. L., Khaw B. A., Nossiff N., O'Donnel S. M., Huang L., Slinkin M. A., Torchilin V. P., *Am.J.Physiol.,* 1991, 261 (suppl.): 60–65, and Torchilin, V. P., Klibanov, A. L., Huang L., O'Donnell S., Nossiff N. D., Khaw B. A., *FASEB J.,* 1992, 6: 2716–2719. However, while these liposomes stayed in the bloodstream longer than PEG-free immunoliposomes, their binding to the target in vitro and in vivo was not improved and in some cases was reduced significantly. See Klibanov A. L., Maruyama K., Beckerleg A. M., Torchilin V. P., Huang L., *Biochim. Biophys. Acta,* 1991, 1062: 142–148 and Klibanov A. L., Khaw B. A., Nossiff N., O'Donnel S. M., Huang L., Slinkin M. A., Torchilin V. P., *Am.J.Physiol.,* 1991, 261 (suppl.): 60–65.

A second attachment procedure is based on the avidin-biotin bridge method originally developed for protein immobilization on regular PEG-free liposomes. See Trubetskaya O. V., Trubetskoy V. S., Domogatsky S. P., Rudin A. V., Popov N. V., Danilov S. M., Nikolayeva M. N., Klibanov A. L., Torchilin V. P., *FEBS Lett.,* 1988, 228: 131–134, and Loughrey H. C., Bally M. B., Cullis P. R. *Biochim. Biophys. Acta,* 1987, 901: 157–160.

Biotinylated phosphatidylethanolamine is incorporated into the liposome membrane, then avidin is added and attached to biotin on liposomes. Free binding sites on avidin are used to bind biotinylated antibodies which are added later. Presence of PEG5000-PE in the composition of biotinylated liposomes does not completely block avidin binding. Klibanov A. L., Maruyama K., Beckerleg A. M., Torchilin V. P., Huang L., *Biochim. Biophys. Acta,* 1991, 1062: 142–148. Therefore, the same sandwich type avidin bridge antibody immobilization is possible for PEG-coated liposomes; Ahmad I., Allen T. M., *Cancer Res.* 1992, 52: 4817–4820. See Ahmad I., Longenecker M., Samuel J., Allen T. M., *Cancer Res.,* 1993, 53: 1484–1488 and Allen T., Agrawal A. K., Ahmad I., Hansen C. B., Zalipsky S., *J. Liposome Res.,* 1993, 4:1.

The third approach takes advantage of bifunctional polyethylene glycol, which possesses reactive groups on both ends of the polymer chain. Klibanov A. L., Huang L., *J. Liposome Res.,* 1992, 2: 321–334. This permits the attachment of antibodies or other protein molecules to liposomes using the same PEG residues that are used to prolong liposome circulation in vivo. Usually, PEG-PE with an active group on the outer tip of PEG is synthesized, purified and incorporated in liposomes. Various chemistries can be applied for this purpose. See Allen T., Agrawal A. K., Ahmad I., Hansen C. B., Zalipsky S., *J. Liposome Res.,* 1993, 4:1–25 and Blume G., Cevc G., Crommelin M. D. J. A. et al., *Biochim. Biophys. Acta* 1993, 1149:180–184.

Many types of chemistry can be used for the attachment of protein molecule to the outer tip of PEG for liposome binding.

Blume and Cevc propose to use PEG with two terminal carboxy residues, one of which is coupled to the primary aminogroup of DSPE. Blume G., Cevc G., Crommelin M. D. J. A. et al., *Biochim. Biophys. Acta* 1993, 1149:180–184. The resulting PEPEG-COOH is incorporated in the liposome, and the terminus is activated by water-soluble carbodiimide. After the activation the protein is added in mild alkaline medium. Up to $2 \cdot 10^{-3}$ moles plasminogen per mol lipid was bound to liposomes by this method; protein coupling yield was about 50%.

Allen and Zalipsky (Allen T., Agrawal A. K., Ahmad I., Hansen C. B., Zalipsky S., *J. Liposome Res.,* 1993, 4:1–25) propose to use carbohydrate moiety of an antibody for the conjugation. The carbohydrate is activated by periodate with the formation of aldehyde groups. Later these aldehydes are reacted with hydrazide-PEG-DSPE incorporated in the liposome membrane. In order to avoid inter-antibody crosslinking (aldehyde to the antibody primary aminogroup) the reaction is performed in mild acidic or neutral conditions.

Allen T., Agrawal A. K., Ahmad I., Hansen C. B., Zalipsky S., *J. Liposome Res.,* 1993, 4:1–25) has described maleimide-PEG-PE, a reagent proposed by Liposome Technology Inc. (FIG. 5C). PEG residue was used as a spacer arm between the lipid anchor and the maleimide group. This chemistry was proposed for antibody binding to the liposome surface more than a decade ago; and at that time, a maleimide bifunctional cross-linking reagent with a short spacer arm was used. Martin F. J., Papahadjopoulos D., *J. Biol. Chem.,* 1982, 257:286–288. A thiol group generated on the antibody molecule or Fab'-fragment, is used to attach to the maleimide residue on tip of the PEG with the formation of a stable thioether bond.

The use of p-nitrophenylcarbonyl-PEG-PE (NP-PEG-PE) as an anchor for the coupling of ligands to liposomes takes advantage of a chemistry which is widely used for protein modification with PEG. Klibanov A. L., *Fifth Princeton Liposome Conference,* Princeton, N.J., 1993. Klibanov A. L., Serbina N., Torchilin V. P., Huang L., *J. Liposome Res.,* 1996, 6: 195–196. Antibodies were simply added to the dispersion of liposomes which contained NP-PEG3350-PE and incubated in a mild alkaline medium.

The compositions of the invention can be formulated into diagnostic compositions for enteral or parenteral administration. These compositions contain an effective amount of the ultrasound agent along with conventional pharmaceutical carriers and excipients appropriate for the type of administration contemplated. Parenteral compositions may be injected directly or mixed with a large volume parenteral composition for systemic administration. Such solutions also may contain pharmaceutically acceptable buffers and, optionally, electrolytes such as sodium chloride.

Formulations for enteral administration may vary widely, as is well-known in the art. In general, such formulations are liquids which include an effective amount of the ultrasound agent in aqueous solution or suspension. Such enteral compositions may optionally include buffers, surfactants, thixotropic agents, and the like. Compositions for oral administration may also contain flavoring agents and other ingredients for enhancing their organoleptic qualities.

The diagnostic compositions are administered in doses effective to achieve the desired enhancement of the ultrasound image. Such doses may vary widely, depending upon the particular agent employed, the organs or tissues which are the subject of the imaging procedure, the imaging procedure, the imaging equipment being used, and the like.

The diagnostic compositions of the invention are used in the conventional manner. The compositions may be administered to a patient, typically a warm-blooded animal, either systemically or locally to the organ or tissue to be imaged, and the patient then subjected to the imaging procedure. Protocols for imaging and instrument procedures are readily found in texts.

The following examples illustrate the specific embodiments of the invention described in this document. As would be apparent to skilled artisans, various changes and modifications are possible and are contemplated within the scope of the invention described.

EXAMPLES

Example 1

In this example we have used the interaction between avidin and biotin as a model system for microbubble targeting. Avidin can be tightly attached to solid surfaces, e.g. to standard polystyrene 35 mm tissue culture plates, by simple incubation. The biotin molecule possesses a carboxyl group, so it can be covalently attached to microbubble shell material, either prior to microbubble preparation or after the shell around the bubbles has been formed.

The avidin solution (2 mg/ml in saline) was incubated in a 35 mm tissue culture-treated polystyrene Petri dish for 1 hour. The avidin solution either filled the dish completely or was deposited in certain areas of the dish using a micropipet, creating target zones coated with avidin. These areas were marked with a waterproof marker in order to improve visual identification of the target. After avidin solution was removed, bovine serum albumin solution (300 mg/ml) was added to block nonspecific binding sites on the dish. Unbound avidin and albumin were removed by a vigorous wash in a stream of tap deionized water. The dish was then filled with normal saline, the microbubble dispersion added, the dish was sealed with mylar self-adhesive tape and inverted. Microbubbles were allowed to float to the dish surface and contact the avidin-coated or the albumin-coated surface to allow avidin-biotin binding to occur. Unless otherwise noted, after completion of the incubation, the dish was inverted back, unsealed, and unbound microbubbles were removed by a wash with a stream of deionized water. In a control study, 1 mg/ml biotin was added to the Petri dish in order to block avidin on the surface. Microbubble attachment to the plate was characterized by optical microscopy as described above.

Selective binding of biotinylated microbubbles with an avidin-coated surface was demonstrated by video microscopy. Microbubbles were not attached to the areas of the dish coated with albumin, and were easily washed away by a stream of water. Targeting of microbubbles to avidin-coated surface was completely inhibited if biotin was added to the medium. In that case, all the microbubbles were removed by a gentle wash.

Binding of the microbubbles to the avidin layer was strongly dependent on the amount of biotin incorporated in the microbubble shell. Firm binding of microbubbles to the avidin layer was demonstrated for microbubbles having 7.5 mol. % biotin-PEG-DSPE in the shell. Microbubbles remained attached to the target even after a vigorous wash under a direct flow of water. A five-fold reduction in the amount of biotin-PEG-DSPE in the shell resulted in much weaker binding of microbubbles to the target surface. While initially microbubbles were still attached to the target, exposure to a direct flow of tap water removed most of the bubbles. Subsequent tenfold reduction of biotin-PEG-DSPE content in the shell reduced the affinity of microbubbles to the target even further. In this case no microbubbles remained on the target surface after the rigorous wash.

We have shown that microbubbles can be selectively targeted via a ligand-receptor system in vitro. Firm binding of microbubbles to avidin-coated surface can be achieved.

Example 2

The fact that microbubbles in suspension are strong ultrasound scatterers may not necessarily imply that microbubbles immobilized on the surface will produce a strong ultrasound contrast effect. To verify that microbubbles on the surface may act as effective ultrasound scatterers, we performed an in vitro imaging study.

A custom built ultrasonic scanning apparatus was used to characterize the reflectivity of the targeted microbubbles. The measurement system consisted of a single PVDF transducer (3.25" focal length, 0.4" diameter, 15 MHz nominal center frequency), which was excited using a broadband pulser (Panametrics 5800). This transducer was also used to receive the backscattered signal, which was then amplified, digitized (Tektronix 2440 oscilloscope), and stored off-line for further analysis. To create C-scanned images the transducer was affixed to a gantry which permitted translation in three spatial dimensions by a high precision motion controller (Aerotech Unidex 12).

The C-scan ultrasound measurement and imaging system was used to insonify microbubbles deposited on a Petri dish. The dish was mounted in a stationary fixture which was submerged in a degassed, room-temperature water bath. The mounting fixture permitted the dish to be tilted at an angle of 100 relative to the axis of insonification, in order to minimize the ultrasonic specular reflection from the dish surface. The center of the dish was placed in the focal zone of the transducer in order to maximize sensitivity and spatial resolution of the image. The peak-to-peak voltage of the backscattered signal was acquired as the transducer was translated in a two dimensional grid measuring 3.5 by 3.5 cm, in steps of 0.05 cm. A two dimensional peak-to-peak image was then generated to show the contrast between regions of high and low reflectivity.

A sharp acoustic image of microbubbles deposited on the target surface was obtained, which corresponded to the pattern of avidin coat on the dish. Presence of microbubbles on avidin-coated areas was verified by optical microscopy.

Example 3

The sensitivity of our custom-built ultrasound laboratory apparatus may be higher than that of a standard medical imaging system. In order to examine the feasibility of targeted microbubble contrast imaging using standard medical equipment, acoustic imaging studies of Petri dishes coated with targeted microbubbles were performed with a medical ultrasound imaging system and a tissue-mimicing ultrasound phantom. The phantom served as a human tissue-equivalent background to permit the ultrasound imaging device receive gain and transmit intensity to be set as they would for imaging of human tissue . This allowed comparison of the signal strength from the targeted microbubbles versus that of the background of human tissue; thereby establishing the relative sensitivity of targeted microbubbles to background tissue.

A plastic tape skirt was placed around the top of a standard ultrasound tissue-mimicking phantom (RMI, 0.5 dB/cm/NnHz)to create a deionized water-filled basin on top of the phantom. The reservoir provided a water path standoff for coupling the imaging probe to the sample A plastic tape skirt was placed around the top of a standard ultrasound tissue-mimicking phantom (RMI, 0.5 dB/cm/MHz) to create a deionized water-filled basin on top of the phantom. The reservoir provided a water path standoff for coupling the imaging probe to the sample. A Petri dish with immobilized microbubbles or a control dish without bubbles was placed inside this water reservoir on top of the phantom. The ultrasound medical imaging system probe was coated with coupling gel and placed in a protective rubber sleeve designed for this purpose. The tip of the probe was then immersed in the reservoir and positioned so that the distance between the tip and the dish would not exceed 5 cm. The probe was positioned at an angle (~45° to the plane of the dish) to avoid specular reflection from the polystyrene surface. Ultrasound images were recorded on video tape. Transmitted intensity and receive gain settings of the medical imaging system were adjusted prior to the experiment, so that a clear view of the tissue phantom could be obtained, i.e. the sensitivity of the imager was in the range generally used for the imaging of patients. Video microscopy of microbubbles on the Petri dish was performed prior to ultrasonic imaging. The fraction of the surface area occupied by microbubbles was calculated using image analysis software.

Bright ultrasound images were clearly visible for the areas of the dish where microbubbles were deposited. Strong ultrasound contrast was obtained for microbubble-coated surface with bubble densities as low as 3.2%. A control polystyrene dish which did not have microbubble coating, produced only marginal ultrasound backscatter. Use of avidin-coated Petri dishes as targets allows direct analysis of the targeted microbubble density on the dish by video microscopy, in parallel with ultrasound imaging. Microbubble-coated avidin spots of 1×2 mm size could be successfully imaged by the ultrasound medical imaging system.

Example 4

Synthesis of Biotinamidoacproyl-PEG3400-DSPE.

Dissolve Biotinamidocaproyl-OSu (Sigma) in chloroform/methanol; add equal molar amount of triethylamine and 0.7 molar amount of NH2-PEG3400-COOH. lot yz-054-2
(Triethylamine has to be free of contamination by primary and secondary amine)

Incubate overnight at room temperature. Check the completion of the reaction by TLC using ninhydrin spray. Evaporate organic solvent to complete dryness, redissolve in saline and dialyse overnight against 3 changes of distilled water (100-fold volume excess, adequate mixing). Lyophilize the dialyzed product until it is completely free of water. Redissolve biotinamidocaproyl-PEG-COOH in chloroform, add 2-fold molar excess of 1-ethyl-3(3-dimethylaminopropyl) carbodiimide and 0.7 molar amount of DSPE solution in chloroform; incubate overnight at room temperature. Evaporate organic solvent in the stream of Ar gas and lyophilize. Purify biotinamidocaproyl-PEG-DSPE from excess PEG and small molecules by dialysis in the Spectra-Por dialysis tubing, MWCO 300,000 or 500,000.

Example 5

Take 20 mg DSPC Avanti lot 180PC87+10 mg PEG40 stearate "Sigma", lot 82H0303; add 10 mg in 2 ml $CHCl_3$ HOOC-PEG3400-DSPE lot 2543-41, add 0.2 ml CHCL3 solution of fluorescein-DHPE "Molecular probes" 0.4 mg, lot 4551-5, cat. F362.

Dissolve, then evaporate all $CHCl_3$ in the stream of Ar gas, lyophilize for 1 hour.

Disperse dried material in 10 ml saline and prepare decafluorobutane-filled microbubbles by sonication (max power XL2020 apparatus, 30 sec.)

After sonication place material in a 20 cc syringe with the stopcock, and centrifuge at 2000 rpm for 2 min 5 times, draining the infranatant liquid and replacing it with saline. Finally, disperse microbubbles in 5 ml 10 mM MES buffer pH 5.

Add to it 100 ul 20 mg/0.9 ml N-hydroxysulfosuccinimide in water.

Add to microbubbles 40 ul of 40 mg/0.8 ml 1-ethyl-3-(3-dimethylaminopropyl) carbodiimide hydrochloride in water and incubate with mixing for 7 minutes.

Prepare mouse antibody, e.g. a non-specific mouse IgG or an anti-ICAM-1 monoclonal antibody: 200 ul IgG in saline (1 mg IgG)+100 ul 1M HEPES pH 7.9

Add 1 ml activated microbubbles to IgG HEPES solution respectively. Incubate on clinical rotator for proper mixing for 2 hours.

Sample flushed with decafluorobutane gas.

Example 6

Preparation of Bac-microbubbles.

20 mg DSPC Avanti #850365 lot 180PC82+20 mg PEG40-stearate (Sigma P3440 barcode 015601)+1 ml (10 mg) chloroform solution of Bac-PEG3400-DSPE (3/27/95) mix, dissolve, evaporate CHCl3 in a stream of Ar gas, lyophilize for 1 hour, add 4 ml 0.9% NaCl isotonic solution, mix, sonicate at "3" setting of XL2020 Heat Systems for 10 minutes, probe tip at the bottom of the vial, vial is hot, start bubbling decafluorobutane PCR lot 94-3003, with sonication, move the tip up, strong foam formation. Cool room temperature water, store at room temperature.
Purification by flotation:

2 ml Bac-microbubbles+20 ml saline in a 3 ml syringe with a stopcock (Bio-Rad polypropylene) placed in a 50 ml tube and centrifuged in a RC-5 centrifuge for 3 min; 2000 rpm. Drain the bottom saline, add 20 ml saline to the foam in the syringe., mix and place in the 50 cc tube.

Centrifugal wash repeated 4 times. After that add 20 ml saline, mix, incubate syringe vertically for 30 min at room temp; drain the bottom small bubbles. Re-mix the top foam in about 2 ml saline and collect through the stopcock.

Coulter counting of the lipopolymer microbubbles. Sample injected in 200 ml Isoton II in the Coulter measuring stand with the propeller stirrer rotating at 2.5 speed.
Binding Study
Surface Preparation.

Corning 35×10 mm Petri dish. Avidin (Sigma#A9275 lot 73H9522, egg avidin, 0.8 mg/ml in water from 950531) 0.8 mg/ml in water, 10 ul deposited on the plate in the form of letter T, incubate for 1 hour. Vigorously wash in the stream of deionized water; Add 0.5 ml of 30% BSA solution, A3424 lot 44H9341, incubate for 15 minutes, rinse with water, fill with 0.9% NaCl Baxter Irrigation solution (about 10 ml).

Add 10 ul microbubbles, lot 2398-55-6, mix with 1 ml micropipet, cover with mylar tape sheet (Sigma T2162 lot 64H1071), seal and invert. Incubate for 15 min. Invert, wash by rinsing with 0.9% NaCl irrigation solution.

Video microscopy with OMT-2 instriument 60×; binding observed. Bubbles at the target after intensive wash in the stream of deionized water and after ULTRASOUND BACKSCATTER IMAGING in vitro, performed by J. Marsh and C. Hall.

Example 7

A 20-kg dog was anesthetized with thiopental, placed on a respirator and continuously anesthetized with isoflurane/air mixture. An IV catheter was used for intravenous injections of the microbubble dispersion. Ultrasound imaging was performed using a HP Sonos 500 ultrasound medical system equipped with a 5 MHz probe. Images of the dog heart before and after injection of contrast were recorded on a video tape. The images were digitized for storage and printing using a Nova Microsonics digitizer station. Dispersion of microbubbles containing biotinamidocaproyl-PEG-DSPE, prepared as described above, was injected intravenously in the dog, and clear ultrasound contrast image of the heart chambers and heart muscle was observed.

Example 8

How to attach antibody to preformed microbubbles:

a carboxyl-PEG-DSPE was incorporated in microbubbles during preparation. Then it was activated with water-soluble carbodiimide (EDC) in the presence of Nhydroxysulfosuccinimide in mildly acidi pH, and antibody added in mildly alkaline HEPES buffer.

Although the invention has been described with respect to specific modifications, the details thereof are not to be construed as limitations, for it will be apparent that various equivalents, changes and modifications may be resorted to without departing from the spirit and scope thereof, and it is understood that such equivalent embodiments are to be included therein.

What is claimed is:

1. An ultrasound contrast media composition comprising a monolayer microbubble shell and a composition of the general formula:

A-P-L, wherein A is an ultrasound contrast agent microbubble-shell binding moiety wherein anchor molecule A of the AP-L structure is anchored to the monolayer microbubble shell at the gas-liquid interface with said A-P-L structure intact during anchoring; P is a polymeric spacer arm having more than 10 monomer units; and L is a ligand, whereby said polymeric spacer arm provides spatial separation of the ligand from said microbubble.

2. The composition of claim 1 wherein the microbubble-shell binding moiety is a lipid, phospholipid, long-chain aliphatic hydrocarbon, lipid multichain, comb-shaped lipid-polymer steroid, fullerene, polyaminoacid, native or denatured protein, aromatic hydrocarbon, or partially or completely fluorinated lipid, the spacer arm is a synthetic polymer or biopolymer, and the ligand is a biomolecule.

3. The composition of claim 2 wherein the microbubble-shell binding moiety is a lipid.

4. The composition of claim 2 wherein the microbubble-shell binding moiety is a phosphatidylethanolamine.

5. The composition of claim 2 wherein the microbubble-shell binding moiety is cardiolipin.

6. The composition of claim 2 wherein the microbubble-shell binding moiety is albumin.

7. The composition of claim 2 wherein the microbubble-shell binding moiety is a polyamine with hydrophobic residues.

8. The composition of claim 1 wherein the spacer arm is a synthetic polymer.

9. The composition of claim 1 wherein the spacer arm is polyoxyethylene.

10. The composition of claim 1 wherein the spacer arm is polyglycerol.

11. The composition of claim 1 wherein the spacer arm is dextran.

12. The composition of claim 1 wherein the spacer arm is polyvinyl pyrrolidone.

13. The composition of claim 2 wherein the biomolecule is a hormone, amino acid, peptide, peptidomimetic, protein, deoxyribonucleic acid (DNA), ribonucleic acid (RNA), lipid, albumin, polyclonal antibody, receptor molecule, carbohydrate receptor binding molecule, monoclonal antibody or aptamer.

14. The composition of claim 13 wherein the biomolecule is an antibody or fragment thereof.

15. The composition of claim 13 wherein the biomolecule is a hormone.

16. The composition of claim 13 wherein the biomolecule is a vitamin.

17. The composition of claim 13 wherein the biomolecule is a peptide.

18. The composition of claim 13 wherein the biomolecule is a peptidomimetic.

19. A method of ultrasound imaging comprising the administration to a patient an ultrasound contrast media composition comprising a monolayer microbubble shell and a composition of the general formula:

A-P-L, wherein A is an ultrasound contrast agent microbubble-shell binding moiety wherein anchor molecule A of the A-P-L structure is anchored to the monolayer microbubble shell at the gas-liquid interface with said A-P-L structure intact during anchoring; P is a polymeric spacer arm having more than 10 monomer units; and L is a ligand.

20. The method of claim 19 wherein the microbubble-shell binding moiety is a lipid, phospholipid, long-chain aliphatic hydrocarbon, lipid multichain, comb-shaped lipid-polymer, steroid, fullerene, polyaminoacid, native or denatured protein, aromatic hydrocarbon, or partially or completely fluorinated lipid, the spacer arm is a synthetic polymer or biopolymer, and the ligand is a biomolecule.

21. The method of claim 20 wherein the microbubble-shell binding moiety is a lipid.

22. The method of claim 20 wherein the microbubble-shell binding moiety is a phosphatidylethanolamine.

23. The method of claim 20 wherein the microbubble-shell binding moiety is cardiolipin.

24. The method of claim 20 wherein the microbubble-shell binding moiety is albumin.

25. The method of claim 20 wherein the microbubble-shell binding moiety is a polyamine with hydrophobic residues.

26. The method of claim 19 wherein the spacer arm is a synthetic polymer .

27. The method of claim 19 wherein the spacer arm is polyoxyethylene.

28. The method of claim 19 wherein the spacer arm is polyglycerol.

29. The method of claim 19 wherein the spacer arm is dextran.

30. The method of claim 19 wherein the spacer arm is polyvinyl pyrrolidone.

31. The method of claim 19 wherein the biomolecule is a hormone, amino acid, peptide, peptidomimetic, protein, deoxyribonucleic acid (DNA), ribonucleic acid (RNA), lipid, albumin, polyclonal antibody, receptor molecule, receptor binding molecule, monoclonal antibody, carbohydrate or aptamer.

32. The method of claim 31 wherein the biomolecule is an antibody or fragment thereof.

33. The method of claim 31 wherein the biomolecule is a hormone.

34. The method of claim 31 wherein the biomolecule is a vitamin.

35. The method of claim 31 wherein the biomolecule is a peptide.

36. The method of claim 31 wherein the biomolecule is a peptidomimetic.

* * * * *